United States Patent [19]

Engel et al.

[11] Patent Number: 6,119,697
[45] Date of Patent: Sep. 19, 2000

[54] DEVICE FOR THE TREATMENT OF MALE AND FEMALE URINARY INCONTINENCE

[75] Inventors: Konrad Engel; Kilian Engel, both of Gaissach, Germany

[73] Assignee: Medi-Globe Vertriebs-GmbH, Germany

[21] Appl. No.: 08/864,367

[22] Filed: May 28, 1997

[51] Int. Cl.[7] ............................................. A61F 5/48
[52] U.S. Cl. ..................... 128/885; 600/29; 128/DIG. 25
[58] Field of Search .................................... 128/885, 886, 128/DIG. 25; 600/29–31; 604/101

[56] References Cited

U.S. PATENT DOCUMENTS

| | | | |
|---|---|---|---|
| 4,911,163 | 3/1990 | Fina | 604/101 |
| 4,976,692 | 12/1990 | Atad | 604/101 |
| 5,724,994 | 3/1998 | Simon | 128/885 |
| 5,785,641 | 7/1998 | Davis | 600/30 |

*Primary Examiner*—Michael A. Brown

*Attorney, Agent, or Firm*—Thomas I. Rozsa; Tony D. Chen; Jerry Fong

[57] ABSTRACT

A device for the treatment of human urinary incontinence with a catheter which can be inserted into the urethra and carries a balloon arrangement which can be filled with fluid to close off the urinary bladder and to hold the catheter in the lumen of the urethra. The fluid can be admitted to and discharged from this balloon arrangement via at least one closed channel running along the catheter wall which is closed off at the distal end of the catheter, and via a valve mounted at one proximal end section of the catheter in inserted condition. The length of the catheter is dimensioned such that its distal end in inserted condition lies within the urethra. A hydraulic actuating mechanism, also located in the lumen of the urinary bladder, is assigned to the self-closing valve. This hydraulic actuating mechanism can be hydraulically actuated by mechanical pressure exerted on an actuating balloon located at the distal end of the catheter which is filled with fluid and linked to the actuating mechanism via a connecting channel (FIG. 1).

55 Claims, 5 Drawing Sheets

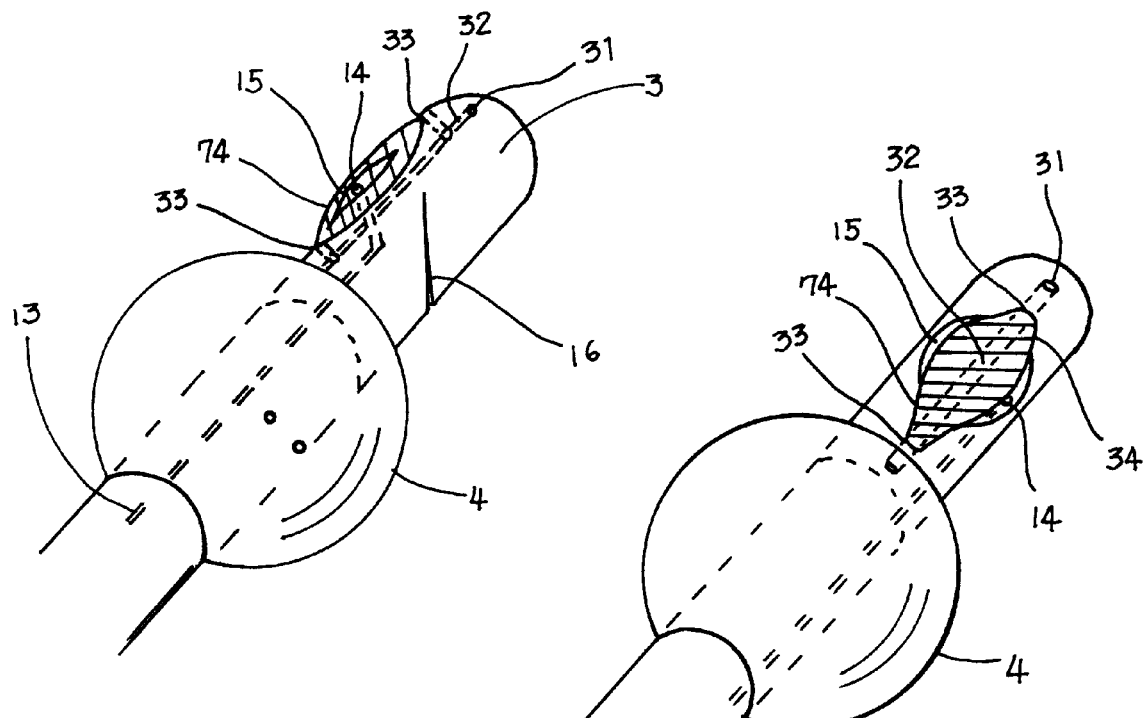
Fig. 3
Fig. 4
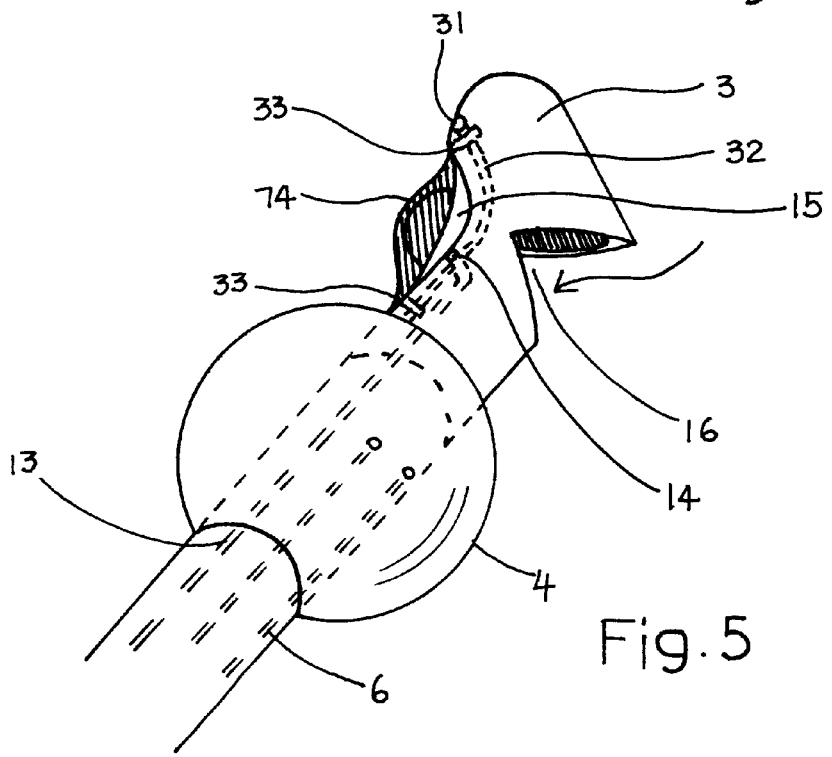
Fig. 5

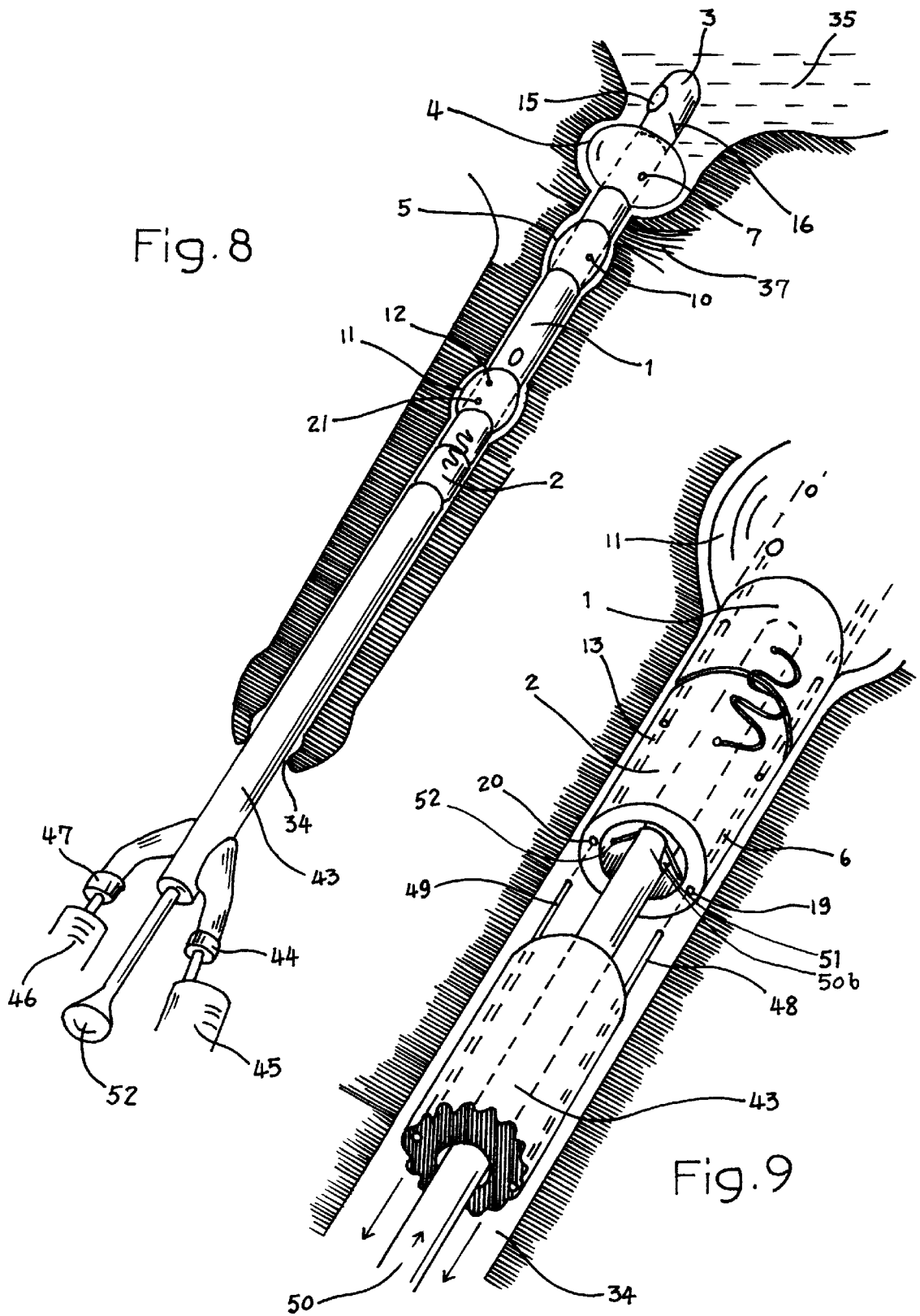

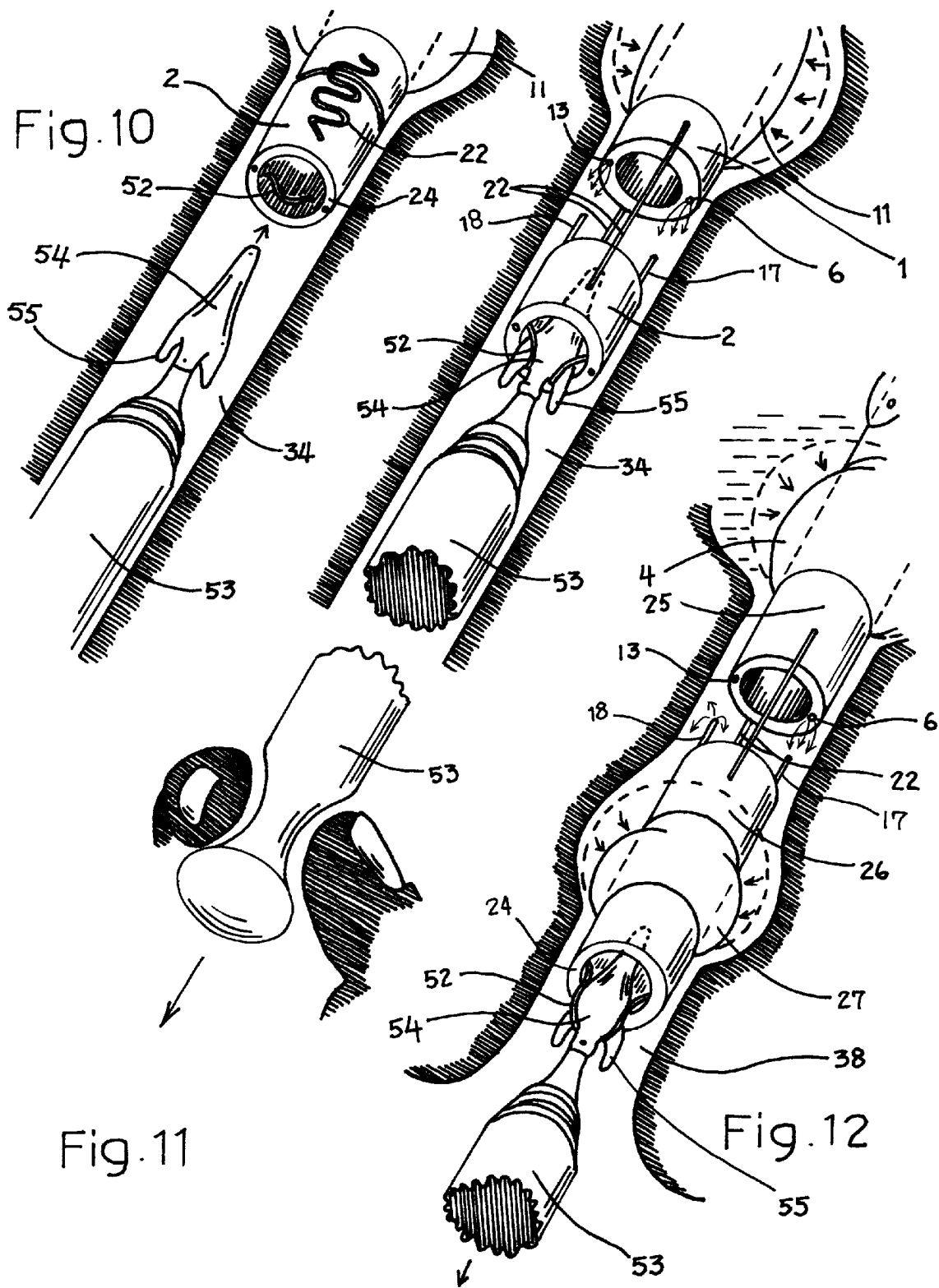

DEVICE FOR THE TREATMENT OF MALE AND FEMALE URINARY INCONTINENCE

BACKGROUND OF THE INVENTION

1. Field of the Invention

The invention relates to a device for the treatment of male and female urinary incontinence according to the preamble of claim 1.

Urinary incontinence is understood as meaning the involuntary loss of urine from the urinary bladder and urethra. The causes are either direct damage to the occlusive mechanism (sphincter muscle) of the urinary bladder, generally as a result of an operation on the prostate gland or by infiltration of a prostate gland carcinoma in men or a sphincter muscle injury as a result of childbirth in the case of women. Further causes of urinary incontinence are nerve damage resulting form metabolic diseases such as e.g. Diabetes mellitus or as a result of traumas to the nerves to the urinary bladder and its occlusive mechanism such as stroke, tumor operations in the pelvic region or injuries to the spinal cord.

In the case of incontinence due to nerve damage, the occlusive mechanism of the bladder can normally no longer be sufficiently opened so that the loss of urine (incontinence) occurs only after maximum filling of the urinary bladder into the volume not completely emptied and uncontrollably. The consequences are not only the urination but also an over-expansion of the urinary bladder and in many cases the reflux of urine up to both kidneys with subsequent kidney damage. The various forms of incontinence generally affect people of advanced age.

2. Description of the Prior Art

A wide range of different methods are already known for treating and overcoming the urinary incontinence, depending on the cause of the incontinence and the sex of the patient; in serious cases, however, these are generally not sufficiently effective or require an operation with or without implantation and is not free from disadvantages in all cases.

In the case of incontinence due to a partial or complete loss of function of the occlusive mechanism of the urinary bladder, particularly in the case of the man, use of a surgically implantable "Scott" artificial bladder sphincter muscle is known (AMS 800 from Messrs American Medical Systems) and can be used. The implant is very expensive and should only be implanted by experienced surgeons. Serious infections or necroses of the tissue surrounding the implant caused by pressure necessitating the removal of the implant again have been repeatedly observed. In women, this form of incontinence can frequently be successfully treated by physical therapy or by a less serious operation without implant.

A further known device for overcoming male incontinence consists of a penis clamp or penoring by which pressure from outside exerts a more or less traumatizing pressure on the penis or urethra. Furthermore there is a risk of slipping in the underwear with subsequent urination.

Furthermore, urine collecting systems worn outside the body with urine bag (urinal) or absorbent media (disposable napkins) are known for both sexes which serve to collect the urine; these result in skin irritation due to the urine, disturbing odor and thus social isolation.

Furthermore, a device for female incontinence is known by which the urinary bladder is emptied via a short catheter protruding out of the urethra by manual actuation of a valve located in the vestibule of the vagina (EP 0407 218 A1). The valve located in the vestibule of the vagina can lead to a colonization of the device with bacteria from the vestibule of the vagina.

More recently, a device for female incontinence has come onto the market under the name "Reliance TM" (U.S. Pat. No. 5,090,424) which consists of an inflatable urethra insert which has to be completely removed several times a day before each emptying of the bladder rather like a tampon and subsequently has to be replaced by a new device, thus making it very costly.

Finally, devices for male incontinence are known with which many of the disadvantages outlined above can basically be avoided (U.S. Pat. No. 4,946,449, DE-OS 4,014,369 U.S. Pat. No. 4,932,938, EP-A 0.265.207, EP 0,543,309 B1). These known devices consist essentially of a catheter which is inserted into the male urethra and carries a balloon at its proximal end which can be filled with a fluid (e.g. water) and thus expanded. This balloon closes off the urinary bladder at the entry to the urethra and prevents the catheter from unintentionally slipping out. At the distal end of the catheter away from the balloon is a second balloon which can be filled with fluid which, when the catheter is in the fitted condition lies outside the bladder sphincter muscle in the urethra and thus prevents the catheter from unintentionally slipping further into the bladder. The length of the catheter is such that when inserted its distal end is completely contained in the penis; a valve is located in the distal end section which can be felt through the wall of the urethra in the penis area. The valve is for example a crocodile valve, lip valve, ball valve or wide valve whose normally closed condition can be changed to the open position by the pressure of the two fingers so that urination is possible. These known valves located in the distal end section of the catheter have several serious disadvantages. The maximum lumen cross-section of a catheter is 5–6 mm which makes the production of lip or crocodile valves miniaturized to these dimensions difficult or even impossible at reasonable cost. A liquid pressure of up to 100 cm water volume is exerted on the closed valve in opening direction by the pressure inside the bladder so that the danger of the valve tipping outward with subsequent loss of function is practically unavoidable. The silicone material used almost exclusively for long horizontal catheters has only a relatively low rubbery-elastic resilience so that lip valves and crocodile valves made of this material require a metal-elastic spring device to return the open valve into a sealing closed position. The production of this spring device in the small dimensions in question here is also technically very complicated. Metallic devices in the catheter wall also result in a hardening of the wall and increase the danger of pressure-related damage to the delicate urethra mucosae. All the above-mentioned valves fitted to the distal end of the catheter result in a significant loss of catheter lumen. This applies in particular to ball valves and slide valves so that no adequate flow of urine is assured in open condition with these valve types. Non-deformable valve elements such as e.g. balls tend to become considerably encrusted due to the substances dissolved in the urine.

SUMMARY OF THE PRESENT INVENTION

The task of the invention is therefore to design a device for treatment and remedying in particular of the male incontinence of the type described at the beginning in such a way that the catheter valve is easy to manufacture, closes reliably with adequate elastic resilience, does not open accidentally even under high pressure inside the bladder, leaves the catheter lumen effectively free in its complete cross-section for free drainage of the urine from the bladder and the insertion of the device into the urethra and its removal from the urethra is simple. In addition, the device should be suitable in its basic principle, but after adaptation to the different anatomical situation of the woman, also for treatment and remedying of the female urinary incontinence.

According to the invention, this task is solved with a device of the type described at the beginning by designing the device in accordance with the characterizing part of claim 1.

The device to which the invention relates is an incontinence catheter which can be completely inserted into the urethra with two sealing balloons, whereby the valve closing off the catheter is located at the proximal end of the catheter extending into the urinary bladder. The valve is opened by finger pressure on an additional balloon filled with fluid (e.g. water) at the distal end of the catheter which can be felt through the wall of the urethra and which is connected to the valve at the proximal end of the catheter by a channel in the catheter wall. The design features of this valve which can be opened and closed by a hydraulic mechanism correspond to no previously known catheter valve and, when the valve is open, lead to no reduction in the drainage lumen of the catheter so that an adequate urinary stream is assured. The miniaturization of a catheter valve to the size of the inner cross-section of the catheter and the associated difficulties in the industrial manufacturing are eliminated. The valve is released from the distal catheter balloon. In addition, the leak-tightness of the closed valve is increased by high pressure inside the bladder.

The attachment of the valve to the proximal end of the catheter as provided for by the invention allows a modified form to be used for women as a completed concealed incontinence catheter with no connection to the body surface for the first time, whereby the occurrence of an infection of the urinary bladder rising from the vestibule of the vagina regularly observed with catheters or external catheter valves can be avoided.

The insertion and positioning as well as the filling of the catheter balloon with a fluid (e.g. water) is performed using a special disposable, sterile insertion rod.

The removal of the incontinence catheter from the urethra is performed using a further disposable, specially formed sterile rod which separates the distal part of the catheter from the proximal part so that the fluid (e.g. water) escapes from the balloon. In principle, the removal of the incontinence catheter from the urethra can also be performed visually through a cystoscope using a conventional urethra foreign-body forceps.

Both the male and the female incontinence catheters are of a relatively simple construction, the technically almost impossible miniaturization of a valve housed in the distal catheter lumen is eliminated so that the incontinence catheters can be manufactured inexpensively as disposable articles. No previously unknown technical processes are required for production. The potential materials are physiologically safe, silicone or latex-based polymers, possibly also with a prior-art hydrophilic silver coating as additional protection against bacterial flora and good compatibility with the mucosae and a monofilament surgical thread material. It is therefore possible to leave the catheter in the lower urinary tract for several weeks or even months.

DESCRIPTION OF THE PRIOR ART

One embodiment for the male and the female urethra is explained in further detail below on the basis of the attached drawings. The drawings show:

FIG. 3 is a schematic view of the identical male and female proximal catheter end with closed valve as a side view.

FIG. 4 is a schematic view of the identical male and female proximal catheter end with closed valve, looking towards the side opposite the valve opening.

FIG. 5 is a schematic view of the identical male and female proximal catheter end with open valve as a side view.

FIG. 8 is a schematic view of the male incontinence catheter with attached insertion rod in the male urethra during the balloon filling phase.

FIG. 9 is a schematic view of the distal section of the male incontinence catheter in the male urethra at the moment of disconnection of the insertion rod.

FIG. 10 is a schematic view of the distal section of the male incontinence catheter in the male urethra during the insertion of the special rod-like extraction device.

FIG. 11 is a schematic view of the distal section of the male incontinence catheter in the male urethra at the beginning of the extraction using the extraction device.

FIG. 12 is a schematic view of the distal section of the female incontinence catheter in the female urethra at the beginning of the extraction using the extraction device.

In the drawings, the same reference symbols have been used for components and characteristics which are identical in the various design forms.

Figure 1:
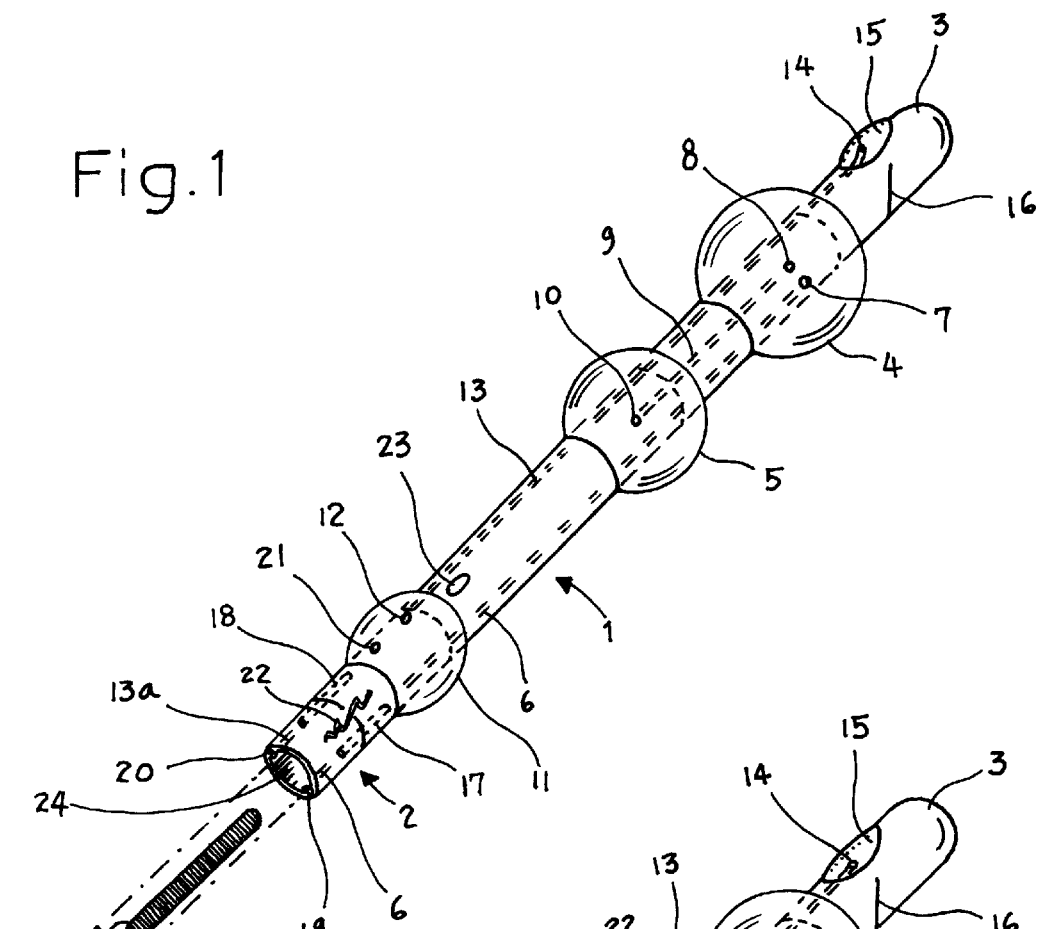
FIG. 1 is a schematic view of the male incontinence catheter with partial illustration of the insertion rod.

FIG. 1 shows the male incontinence catheter drawn approximately in the scale 1:1, made of elastic material, e.g. silicone. The proximal end of the catheter carries a balloon 4 with a capacity of about 10 ccm. Another balloon 5 which has a capacity of about 2–3 ccm is located at a short distance distally to it. A channel 6 which runs longitudinally in the wall of the catheter ends with an opening 7 within the balloon 4. Balloon 4 is connected with balloon 5 by another opening 8 and a short longitudinal channel 9 along the catheter wall and another opening 10. The opening 10 has a smaller cross-section than the openings 7 and 8 as a result of which, balloon 5 fills more slowly with fluid in comparison to balloon 4.

At the distal end of the proximal catheter section 1 is a third balloon 11 with a capacity of about 2 ccm. The opening 12 of the catheter wall connects this balloon 11 by a longitudinal channel 13 along the catheter wall and an opening 14 with a small semi-balloon 15 (capacity: 0,5–1 ccm) at the proximal end 3 of the catheter. This semi-balloon 15 is part of the hydraulic mechanism which opens and closes the opening 16 of the valve that drains the urinary bladder. This opening 16 is made by a diagonal cut into the wall of the proximal end 3 of the catheter. In a closed position, the sealing edges of the openings 16 have to be waterproof.

The two catheter sections 1 and 2 are connected by two small plastic pipes 17 and 18. Additionally, the plastic pipe 17 connects the longitudinal channel 6 with an "elastic puncture valve" 19 at the front side of catheter section 2. The small plastic pipe 18 bridges channel 13a which runs from the puncture valve 20 to a wall opening 21 within balloon 11. This opening 21 has a wider cross-section that the other opening 12 within balloon 11 in order to avoid overfilling and overstretching of semi-balloon 15 when filling balloon 11 with fluid.

Two loose threads 22 (one thread is not shown) which are attached respectively to the walls of the catheter sections 1 and 2 connect these catheter sections additionally.

Proximally to the distal balloon 11, the catheter wall has two big holes 23 to drain the secretion produced by urethral glands. Besides this, there is a cross-wise running thread 52 according to FIG. 9 attached to the inside of lumen 24 of the distal catheter section 2. This thread 52 is necessary for the insertion and extraction of the catheter into, respectively out of the urethra.

Figure 2:
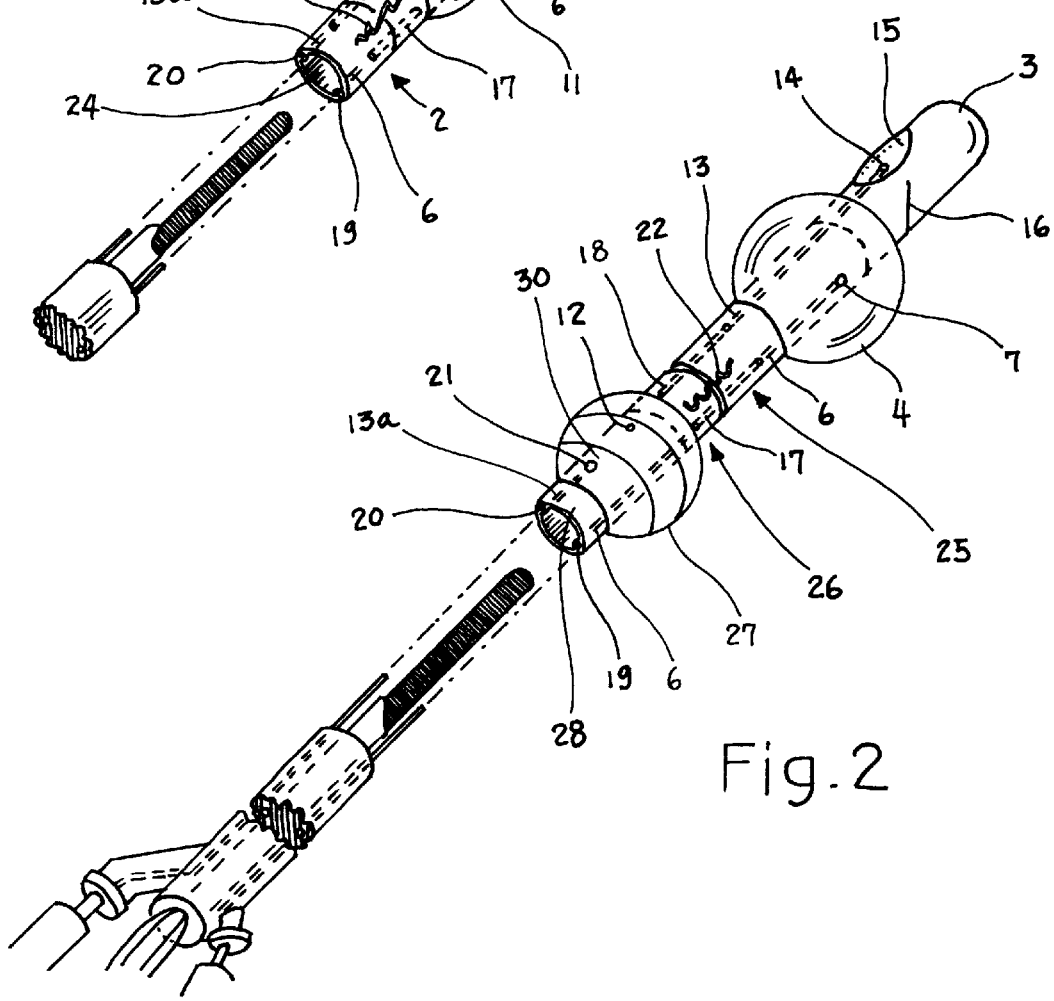
FIG. 2 is a schematic view of the female incontinence catheter with partial illustration of the insertion rod.

FIG. 2 shows the female incontinence catheter drawn approximately in the scale of 1:1, but the distance between the two balloons 4 and 27 should be as short as possible (e.g. 1 cm or less), therefore being shorter than shown in FIG. 2. This detail shortens the whole length of the female catheter. The catheter is put together by two disconnectable sections, a proximal section 25 and a distal section 26. The proximal section 25 carries first balloon 4 with a capacity of 5–8 ccm. From the distal end 28 of the catheter a longitudinal channel 6 runs to an opening 7 within the proximal balloon 4. A second balloon 27 is located at the distal section 26 which is connected to a small semi-balloon 15 (capacity: 0,5–1 ccm) at the proximal end 3 by an opening 12 a channel 13 and an opening 14. The balloon 27 has a capacity of 2–3 ccm. Semi-balloon 15 is the main part of hydraulic mechanism which actuates the opening 16 of the valve.

The distal catheter section 26 is again connected to the proximal section 25 by two small plastic pipes 17 and 18. Plastic pipe 17 connects channel 6 with an "elastic puncture valve" 19. Plastic pipe 18 bridges channel 13. Balloon 27 fills through an "elastic puncture valve" 20 over channel 13a and an opening 21. The opening 21 has again a wider cross-section than the opening 12 within balloon 27.

Figure 7:
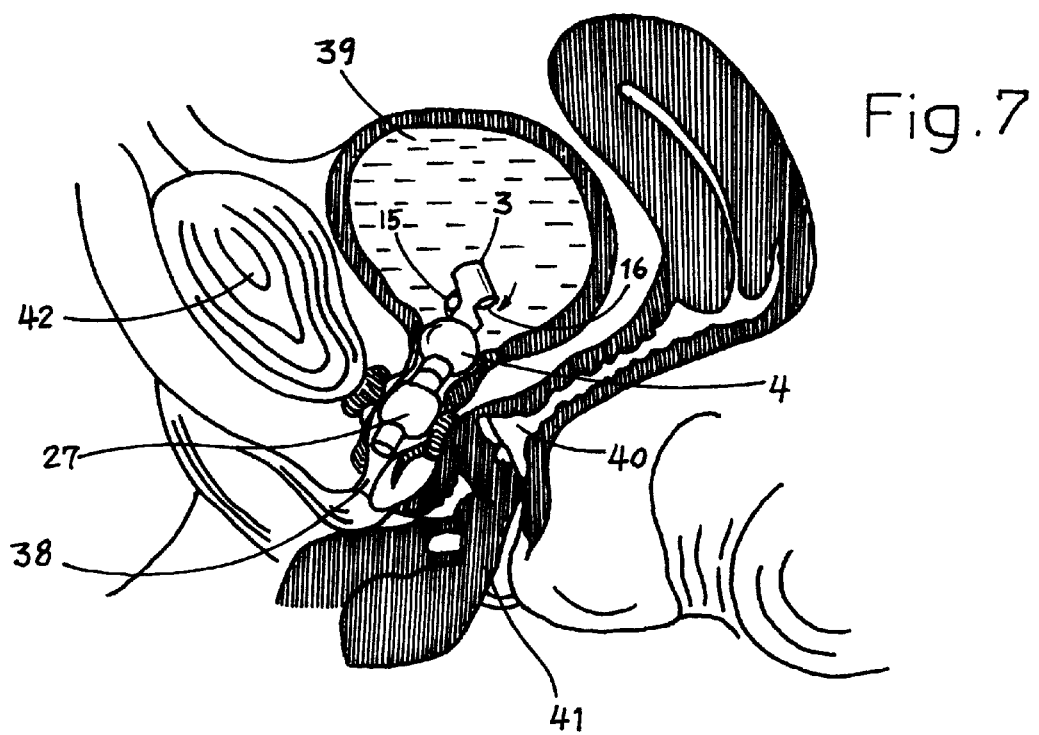
FIG. 7 is a schematic view of the female incontinence catheter to which the invention relates in the female urethra with the valve open.

The surface of balloon 27 has a profile in form of two to four cross-wise running ribs or batons to prevent dislocation of the female incontinence catheter inside the short female urethra 38, when balloon 27 is compressed according to FIG. 7.

FIGS. 3, 4 and 5 show details and function of the valve at the proximal end 3 of the catheter, which is the same in both the male and female incontinence catheter. Inside the wall of the proximal end 3 is a resilient elastic plastic baton 32 (similar to a fish bone) which is put in its position through a hole 31 within the catheter tip 3. Two threads 33 are tied around the two ends of baton 32 which attach a rombic-shaped piece of non-elastic tissue 74 to the baton 32. This piece of tissue 74 covers semi-balloon 15 rather tightly. The small semi-balloon 15 fills when pressure is exerted on balloon 11 of the male incontinence catheter according to FIG. 1 and on balloon 27 of the female incontinence catheter according to FIG. 2. In this moment tissue 74, which covers semi-balloon 15 causes traction on both ends of baton 32. Baton 32 bends towards balloon 15 like a hunting bow. Opening 16 of the valve opens and drains the urinary bladder through the lumen of the catheter. When the bladder is empty, the pressure on balloon 11 according to FIG. 1, respectively on balloon 27 according to FIG. 2 is removed and the small semi-balloon 15 collapses. The resilient elastic force of baton 32 allows the tip 3 of the catheter to return to its original shape and thereby closes valve 16.

Figure 6:
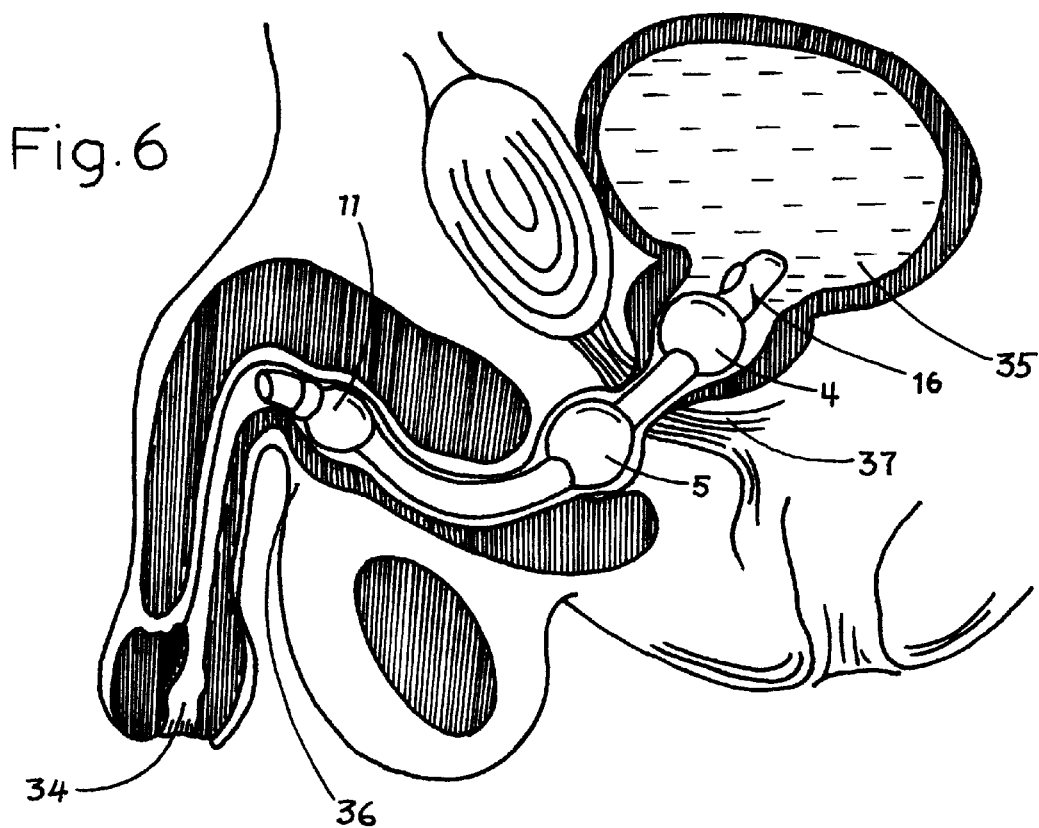
FIG. 6 is a schematic view of the male incontinence catheter to which the invention relates in inserted position in the male urethra, whereby the catheter valve extending into the urinary bladder is closed.

FIG. 6 shows a simplified drawing of the anatomy of the male urethra 34 with a full urinary bladder 35 and a male incontinence catheter according to FIG. 1 with a closed valve 16.

FIG. 7 shows a simplified drawing of the anatomy of the female urethra 38 and a full urinary bladder 39 with a female incontinence catheter according to FIG. 2. An index finger 41 is inserted into the vagina 40 which in turn actuates mechanical pressure on balloon 27 by pressing balloon 27 against the symphysis 42 (which is part of the bones of the pelvis). By this pressure semi-balloon 15 is filled and valve 16 is opened.

FIG. 8 shows the male incontinence catheter according to FIG. 1 in the moment of the insertion of the catheter into the male urethra 34 with a special, rigid, sterile insertion rod 43 which is connected to the catheter.

The insertion rod 43 has two normal catheter valves 44 and 47 at its distal end. Balloon 4, which seals the bladder is already filled with fluid with help of a normal syringe 45 attached to valve 44, and is set into the right position above the sphincter muscle 37 by light traction on the insertion rod. Fluid now flows slowly through a small opening 10a into the second sealing balloon 5. (In this case, you see a simplified version: channel 9 according to FIG. 1 is missing.)

After positioning the catheter correctly, balloon 11 is filled with fluid with the help of a syringe 46 which is attached to valve 47 of the insertion rod 43. To avoid overfilling and straining of semi-balloon 15 and valve 16, the opening 21 has a wider cross-section than the opening 12, both of which are inside balloon 11. (if balloon 11 is filled gently with fluid it may be possible to do away with one of the openings within balloon 11).

FIG. 9 shows a partial view of the distal section of the male incontinence catheter according to FIG. 1 in the male urethra 34 in the moment of disconnection of the insertion rod 43. Inside the insertion rod 43 is a longitudinal, shiftable, rigid nucleus 50 which protrudes so far into the distal end of the catheter that section 1 and section 2 are stabilized and do not become disconnected when the catheter is inserted into the urethra 34. The proximal end 50b of the nucleus 50 has a semi-circular cross section and a notch 51. This notch 51 holds a thread 52, which is attached diagonally in the lumen of the distal section 2 of the catheter. This is necessary to keep the catheter in its position within the urethra 34 while removing the insertion rod 43. After the outer shell of the insertion rod 43 with its two canulas 48 and 49 has been retracted slightly, the whole insertion rod 43 can be removed.

The female incontinence catheter according to FIG. 2 is inserted in the same way except that the insertion rod is somewhat shorter.

FIG. 10 and FIG. 11 show a partial view of the removal of the male catheter according to FIG. 1 out of the male urethra 34 with a special, sterile, rigid extraction rod 53. This extraction rod 53 with its harpoon-like rounded proximal tip 54 is inserted blindly into the urethra 34 and into the open lumen 24 of the distal section 2 of the catheter. When removed, the harpoon-like tip 54 catches with its two to four barbs 55 the thread 52 which is attached diagonally in the lumen 24. Further removal of the extraction rod 53 causes a disconnection of section 1 and 2, and a removal of the small plastic pipes 17 and 18 out of the channels 6 and 13. The fluid streams out of the channels and out of the balloons 4,5 and 11 according to FIG. 1.

The two threads 22 keep a loose connection between section 1 and section 2, so that the whole catheter can be totally extracted out of the urethra 34 by further traction of the extraction rod 53.

FIG. 12 shows a partial view of the removal of the female catheter according to FIG. 2 out of the female urethra 38.

The extraction rod 53 has the same construction as shown in FIGS. 10 and 11, but somewhat shorter. The technique of the removal of the female catheter is the same as shown in FIGS. 10 and 11 with one important difference. By the fact that the female urethra 38 has a wider cross-section than the male urethra, it is possible to retract the full balloon 27 slightly up to the point till the sections 25 and 26 are disconnected and the small pipes 17 and 18 are removed out of the channels 6 and 13. The fluid streams out of the channels and out of the balloons 27 and 4 according to FIG. 2. By further traction of the extraction rod 53 the catheter is extracted totally out of the urethra 38. (The plastic pipes 17 and 18 of the female catheter should be rather short so that a gentle traction at the beginning is sufficient to disconnect the two sections 25 and 26).

n.b. the Distal hydraulic balloon 11 according to FIGS. 1 and 27 according to FIG. 2 have a rather low capacity of 2–3 ccm. If these balloons have a flat oval shape, it might be possible to fill these balloons with fluid during the manufacturing. By doing this, the catheters, both male and female, could be inserted with a "closed hydraulic system". This would enable a simplified method of production. The cross-section of the "hydraulic balloons" 11 and 27 with fluid should not be wider than 20 F for the male, and 22 F for the female catheter.

DESCRIPTION OF THE PREFERRED EMBODIMENT

In accordance with FIG. 1, the device to which the invention relates consists of a hose-like or tubular catheter consisting of a proximal part 1 and a distal part 2, which can be removed from the proximal part, both e.g. of silicone, the length of which is so dimensioned that in the inserted condition its distal part 2 lies within the male urethra 34 (FIG. 6) while its proximal end 3 extends into the lumen of the urinary bladder 35 (FIG. 6). In the vicinity of the proximal end 3, a first balloon 4 is permanently attached to the outside of catheter part 1. A short distance distally from it, a second (smaller) balloon 5 is fixed to the outside of catheter part 1. From the distal end of catheter part 2, a channel 6 (shown in dotted lines) runs through the wall of part 2 and of part 1 which ends inside the proximal balloon 4 through an opening 7 provided in the wall of the catheter. Alongside opening 7, a second opening 8 leading into balloon 4 exists in the wall of part 1 from which a connecting channel 9 (shown in dotted lines) also runs through the catheter wall to the middle balloon 5 and ends there in an opening 10 which has a significantly smaller cross-section than the openings 7 and 8 of proximal balloon 4. As a result, filling of balloon 5 is delayed compared with balloon 4 when a fluid (e.g. water) is admitted to balloon 4 via channel 6.

Near the distal end of catheter part 1 is a third balloon 11 connected to the wall of part 1. The opening 12 in the catheter wall connects this balloon 11 via a proximal channel 13 running through the catheter wall and an opening 14 at the proximal end of the catheter 3 with a small semi-balloon 15 permanently connected to the wall of part 1 which forms the main component of an opening mechanism of the valve opening 16. The valve opening 16 is defined by sealing lips produced by a diagonal cut in the wall of the proximal end of the catheter 3 which are pressed together and when closed are pressed even tighter together by the pressure inside the bladder.

The distal catheter part 2 is pushed onto catheter part 1. Two small-bore plastic pipes 17 and 18 serve as connecting elements. In addition, the small plastic pipe 17 links the longitudinal channel 6 with an elastic "puncture valve" 19 in front end of catheter part 2. The small plastic pipe 18 extends a longitudinal channel 13a running from a puncture valve 20 in the front end of catheter part 2 which runs in the wall of part 2 and ends in an opening 21 inside the balloon 11. Two loose threads 22 (one thread is not shown), one end of which is anchored in the wall of the disconnectable distal part 2 and the other end in the wall of the proximal part 1, create an additional loose connection between the two catheter parts 1 and 2. Proximally to the distal balloon 11, the catheter wall of part 1 has one or two relatively large openings 23 to drain the secretion from the proximal urethra into the lumen 24 of the catheter.

As can be more clearly seen in FIG. 9 and is not shown in FIGS. 1 and 2 for the sake of clarity, a thread 52 is securely anchored to the distal end of catheter part 2 and runs cross-wise across its lumen. This thread 52 serves, as explained in more detail further below, to insert the catheter to which the invention relates into and to extract the catheter from the urethra.

In accordance with FIG. 2, the female device to which the invention relates consists of a hose-like or tubular catheter, e.g. of silicone, the length of which is so dimensioned that in inserted condition its distal end 28 lies within the female urethra 38 (FIG. 7) while its proximal end 3 extends into the lumen of the urinary bladder 39. The catheter consists of two disconnectable parts, a proximal part 25 and a distal part 26.

A first balloon 4 is permanently attached to the outside of the proximal part 1. From the distal end 28 of the distal catheter part 26, a channel 6 runs through the wall of part 26, continues through the wall of the proximal part 25 and enters the proximal balloon 4 through an opening 7 provided in the wall of catheter.

A second balloon 27 is permanently connected to the wall of the distal catheter part 26. The opening 12 in the catheter wall connects this balloon 27 via a channel 13 running through the catheter wall and an opening 14 at the proximal end 3 of the proximal catheter part 25 with a small semi-balloon 15 permanently connected to the wall of the catheter part 25 which forms the main component of an opening mechanism of the valve opening 16.

The distal catheter part 26 is pushed onto the proximal catheter part 25. Two small-bore plastic pipes 17 and 18 again serve as connecting elements. In addition, the small plastic pipe 17 links the longitudinal channel 6 with an elastic "puncture valve" 19 in front end of part 26. The small plastic pipe 18 extends a longitudinal channel 13a running from a puncture valve 20 in the front end of catheter part 26 which ends in an opening 21 inside the balloon 27. Two loose threads 22 (one thread is not shown), one end of which is anchored in the wall of the distal catheter part 26 and the other end in the wall of the catheter part 25, create an additional loose connection between the two catheter parts 25 and 26.

In order to prevent a change in position of the incontinence catheter in the female urethra 38 when actuating the hydraulic release mechanism to open the valve opening 16 by compression of the balloon 27 which can be felt through the front vaginal wall 40 (FIG. 7), the balloon has between two and four strip-like, circular bulges or ribs 30 running transversely to the longitudinal axis of the incontinence catheter. The bulges 30 can also, if required, be replaced by other structures with the same function (not illustrated) which change the surface of the balloon 27.

FIGS. 3, 4 and 5 show details and the function of the drain valve into the catheter lumen located at the proximal catheter end 3 which is the same in both the male and female incontinence catheters to which the invention relates.

Embedded in the wall of the proximal catheter end 3 under the pretension closing valve 16 is a resilient elastic baton of metal or plastic 32 running in longitudinal direction which is fitted in its position through an opening 31. Two threads 33 are tied around the two ends of baton 32 which fasten a roughly diamond-shaped piece of fleece made from a human tissue-compatible material flat over the catheter end 3 and the semi-balloon 15. The fleece 74 is wider at its longitudinal centerline in order to prevent it slipping off the semi-balloon 15 during its subsequent expansion which is described below. As a fluid (e.g. water) is admitted under pressure via the channel 13 into the wall of the device and through the opening 14 into the semi-balloon 15, the small semi-balloon 15 is filled and thus expands.

When pressure is applied to the balloon 11 of the male device in accordance with FIG. 1 which can be felt through the wall of the male urethra 34 (FIG. 6) or when pressure is applied to the balloon 27 of the female device in accordance with FIG. 2 which can be felt through the front wall of the vagina 40 (FIG. 7) and through the wall of the female urethra 38, the pressure of the fluid (e.g. water) in channel 13 of the male or female device increases.

As a result of this increase in pressure, the semi-balloon 15 bulges and the more or less non-elastic fleece 74 covering the small semi-balloon 15 causes traction to be applied to the two threads 33 attached to the ends of the flexible baton 32 so that the plastic baton bends towards the small semi-balloon 15 like a hunting bow together with the wall of the proximal end 3 of the catheter. At the same time, the valve 16 on the opposite side of the proximal catheter end 3 opens, rather like the face mask of a knight's helmet from the Middle Ages, and allows the urine to flow in from the urinary bladder 35 or 39. When the urinary bladder 35 or 39 is empty and the pressure on the balloon 11 (FIG. 1) or 27 (FIG. 2) is relieved, the small semi-balloon 15 is emptied by the fluid (e.g. water) flowing back via channel 13 into the balloon 11 or 27. This is effected in particular by the elastic resilience of the elastic baton 32 as the bending strain in the baton is relieved and it returns to its original shape. The proximal catheter end 3 thus returns to its original form and the valve 16 is closed under the pressure exerted by the baton 32.

FIG. 6 shows a schematic view of the anatomy of the male urethra 34 with a full urinary bladder 35 with the male device I in accordance with FIG. 1 inserted into the male urethra 34, whereby the valve opening 16 extending into the urinary bladder is closed. The balloon 11 used for the hydraulic opening of the valve opening 16 lies roughly at the level of the scrotum root 36. The urinary bladder sealing balloons 4 and 5 of the device are shown in filled condition above and below the area of the sphincter muscle 37.

FIG. 7 shows a schematic view of the anatomy of the female urethra 38 with a full urinary bladder 39 with the female device 1 in accordance with FIG. 2 inserted into the female urethra 38. The proximal part 25 of the device (FIG. 2) with the sealing balloon 4 and the proximal end 3 extending into the full urinary bladder. The index finger 41 inserted into the outer opening of the vagina 40 compresses the balloon 27 of the device which can be felt through the front wall of the vagina 40 and the rear wall of the urethra 38, whereby the symphysis 42 (which is part of the bones of the pelvis) serves as an abutment for the pressure. The semi-balloon 15 of the proximal catheter end 3 thus bulges and the valve 16 is opened so that the urine can flow into the lumen of the device in the direction of the arrow.

FIG. 8 shows a schematic view of the male device just inserted into the male urethra 34 (but not yet secured in place) with a special rigid or partially elastic, sterile fitted filling and insertion rod 43, whereby the proximal end 3 extends into the urinary bladder 35 with the empty semi-balloon 15 and thus closed valve 16. The sealing balloon 4 of the proximal part 1 has already been filled with fluid (e.g. water) using a syringe 45 fitted to the valve 44 of the insertion rod 43 which corresponds to a prior art catheter valve. The second sealing balloon 5 of the proximal catheter section 1 has not yet been expanded.

A possible simpler design variant of the male device is indicated; this consists in the balloon 4 and balloon 5 being linked in a straight line by a single channel 6 already existing in the wall of the device, thus eliminating channel 9 (FIG. 1), whereby the single opening 7 in the catheter wall inside the balloon 4 has a significantly larger cross-section than an opening 10a of the balloon 5 connected to channel 6 so that after filling balloon 4, a short time remains to allow the device to be adjusted to the proper position by pulling it back slightly with slight tension on the insertion rod 43.

The balloon 4 is thus positioned above the natural constriction of the urethra 34 in the area of the sphincter muscle 37 which still exists even in incontinent persons. Only then is the balloon 5 slowly filled with fluid (e.g. water), as shown in the design in FIG. 1, through the throttling effect of opening 10a. The additional wall opening 8 within the balloon 4 and the corresponding channel 9 shown in FIG. 1 do not exist here. In order to prevent a change in position of the incontinence catheter in the female balloon 11 is filled with a few milliliters of fluid (e.g. water) with the help of a syringe 46 which is attached to a valve 47 on the insertion rod; this valve is identical with the valve 44. In order to avoid a simultaneous maximum filling of the semi-balloon 15 at the proximal end of the device, the openings 21 and 12 in the wall of the proximal catheter section 1 inside the balloon 11 can have different cross-sections such that opening 12 has a slightly smaller cross-section than opening 21.

FIG. 9 shows a schematic partial view of the distal section of the male incontinence catheter in accordance with FIG. 1 in the male urethra 34 at the moment of disconnection of the insertion rod 43 from the distal section 2 of the incontinence catheter after the balloons 4, 5 and 11 (FIG. 8 and FIG. 1) have already been filled by injection of fluid (e.g. water) via the valves 44 and 47 through canula-like, round-tipped continuations 48 and 49 of the insertion rod 43 and through the elastic puncture valves 19 and 20 in the distal section of the device. (Balloons 4 and 5 not shown)

Inside the insertion rod 43 is a longitudinally shiftable rigid nucleus 50, the front end 50b of which can be inserted into the lumen of the catheter far enough that it passes over the joint between parts 1 and 2 (shown as a dotted line in FIG. 9) so that the joint is stabilized and the small pipes 17, 18 are protected from bending when the catheter is inserted. In the embodiment, the front end section 50b has a semi-circular cross-section in order to be able to pass the thread 52 running cross-wise through the lumen of the distal part 2 of the device and securely anchored to the wall of the distal part 2 of the device. At the rear end of the end section of 50b, the resulting rod shoulder has a notch 51 which holds the thread 52. A dislocation of the device during the extraction of the insertion rod 43 due to the adhesion of the canulae 48 and 49 of the insertion rod in the puncture valves 19 and 20 necessary at the start of positioning of the device in the male urethra 34 is avoided by exerting slight pressure on the outer end 50a of the nucleus 50.

Positioning of the female incontinence catheter in accordance with FIG. 2 in the female urethra 38 (FIG. 7) is performed in the same way (not illustrated) using an identical or slightly shorter insertion rod 43 in accordance with FIG. 8.

FIGS. 10 and 11 show schematic partial views of the male incontinence catheter in accordance with FIG. 1 during the process of removal from the male urethra 34. A special rigid or partially elastic sterile extraction rod 53 with its harpoon-like rounded tip 54 is first inserted blindly into the male urethra 34 and then pushed forward into the open lumen 24 of the distal part 2 of the device. When the extraction rod 53 is then pulled back, one of two or more rounded barbs 55 of the tip 54 catches in the thread 52 running cross-wise through the lumen of the distal part 2 and securely anchored in its walls. Further removal of the extraction rod 53 (the removal direction is indicated by an arrow in FIG. 11) causes the distal part 2 to be disconnected from the proximal part 1 of the device. The two small plastic pipes 17 and 18 are removed from the lumina of the wall channels 6 and 13. The balloons 4, 5 and 11 can empty via the free openings of the channels 6 and 13 in the wall of the proximal part 1 of the device into the lumen of the urethra 34 (indicated by arrows). The two threads 22 which are firmly anchored in the walls of parts 1 and 2 hold parts 1 and 2 together. The whole catheter can now be easily extracted from the male urethra 34 by further traction on the extraction rod 53.

FIG. 12 shows a schematic partial view of the female incontinence catheter in accordance with FIG. 2 during the process of removal from the female urethra 38. The extraction rod 53 is fundamentally identical with or shorter than that shown in FIGS. 10 and 11. When this extraction rod 53 is inserted into the female urethra 38 and then pushed forward into the open lumen 24 of the distal part 26 of the device, the rounded barbs 55 of the harpoon-like tip 54 of the extraction rod 53 catch in the thread 52 in the lumen 24 of the distal part 26. Further removal of the extraction rod 53 separates the distal part 26 from the proximal part 25. The two fluid-filled balloons 27 and 4 empty via the small plastic pipe 18 forming part of the wall channel 13 which is securely attached to part 26 of the device and via the then open lumen of the wall channel 6 in the proximal part 25 of the catheter (indicated by arrows) into the female urethra 38. Further traction on the extraction rod 53 (the direction of the traction is indicated by an arrow) removes the female incontinence catheter from the female urethra 38.

In principle, the process of extraction of the male incontinence catheter in accordance with FIG. 1 from the male urethra 34, FIGS. 10 and 11, and of the female incontinence catheter in accordance with FIG. 2 from the female urethra 38, FIG. 12, can also be performed visually through a cystoscope using a conventional urethra foreign body forceps.

The emptying of the balloons 4, 5 and 11 or 4 and 27 necessary for the extraction is also possible via a modified construction which is not illustrated in the drawings.

With this construction it is planned that the corresponding channels 6 or 13 are each accessible via a "window" facing towards the lumen of the catheter, expediently mounted on the distal end of the catheter, which can be deliberately destroyed for the purpose of extraction. This window can be an opening closed off by a membrane until it is destroyed by means of a probe or urethra foreign-body forceps.

During the course of the invention, it is possible to deviate from the embodiments described above. For example, the invention is not limited to the form of the valve 16 produced by a diagonal cut at the catheter end 3. In principle, any type of valve is conceivable which open up an inlet opening at the catheter end 3 by hydraulic actuation. Furthermore it could be considered protecting the fleece 74 which serves as a transmission element for opening the valve 16 by bending the resilient elastic baton 32 by means of a membrane or similar structure against the negative effects of the urine. Such a membrane can more or less surround the catheter end 3 in the area of the fleece 74, but without having a mechanical reaction on it. Instead of the fleece 74, any surgical material can be used which is capable of transmitting a tractive force to the resilient elastic baton 32 with no noticeable elastic expansion.

Furthermore, it is not absolutely essential to fill the actuating balloon 11 or 27, with which the semi-balloon 15 of the actuating mechanism is caused to bulge, with fluid only after insertion of the catheter. Instead the fluid can be contained from the outset in the closed-center system formed by the actuating balloon 11 or 27, the channel 13 and the semi-balloon 15.

Defined in detail, the present invention is a device for the treatment of human urinary incontinence comprising: a catheter which can be inserted into the urethra and carries a balloon arrangement which can be filled with fluid to close off the urinary bladder and to hold the catheter in the lumen of the urethra, the fluid can be admitted to and discharged from this balloon arrangement via at least one channel running along the catheter wall which is closed off at the distal end of the catheter, and via a self-closing valve mounted at one end section of the catheter, whereby the length of the catheter is dimensioned such that its distal end in inserted condition lies within the urethra and the valve can be actuated by mechanical pressure exerted from outside the urethra on the same, characterized in that the valve is installed in the proximal end section which, with the catheter in inserted condition, lies within the lumen of the urinary bladder, in that the proximal end section carries a hydraulic actuating mechanism for opening the valve and in that the actuating mechanism can be hydraulically pressurized by mechanical pressure exerted on an actuating balloon located on the distal end section of the catheter which is filled with fluid and connected to the actuating mechanism via a connecting channel.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A device for the treatment of human urinary incontinence comprising: a catheter which is inserted into the urethra and carries a balloon arrangement which is filled with fluid to close off the urinary bladder and to hold the catheter in the lumen of the urethra, the fluid being admitted to and discharged from the balloon arrangement via at least one channel running along the catheter wall which is closed off at the distal end of the catheter, and via a valve mounted at one end section of the catheter located in the urinary bladder, whereby the length of the catheter is dimensioned such that its distal end in the inserted condition lies within the urethra and the valve is actuated by mechanical pressure exerted from outside the urethra on an actuating balloon located at the distal end of the catheter, characterized in that the valve is installed in the proximal end section which, with the catheter in the inserted condition, lies within the lumen of the urinary bladder, in that the proximal end section carries a hydraulic actuating mechanism for opening the valve and in that the actuating mechanism can be hydraulically pressurized by mechanical pressure exerted on the actuating balloon located on the distal end section of the catheter which is filled with fluid and connected to the actuating mechanism via a connecting channel.

2. The device in accordance with claim 1 wherein said valve is an elastically resilient flap valve which can be lifted from its valve seat by said actuating element of the actuating mechanism.

3. The device in accordance with claim 1 wherein said actuating mechanism further comprises a non-elastic traction element which is deflected by the actuating element.

4. The device in accordance with claim 3, characterized in that the actuating element is a hydraulically expandable membrane, one side of which can be hydraulically pressurized via the connecting channel and whose expansion deflects the spanned traction element.

5. The device in accordance with claim 3, characterized in that the traction element is a traction band tightly covering the expandable membrane, the ends of which are permanently connected to the areas of the proximal end section assigned to the sealing lips of the valve.

6. The device in accordance with claim 1 wherein said valve can be closed off by a resilient elastic section of the proximal end section.

7. The device in accordance with claim 6, characterized in that the resilient elastic section is formed by a flexible elastic baton located in the catheter wall.

8. The device in accordance with claim 1 wherein said actuating mechanism is surrounded by a protective membrane.

9. The device in accordance with claim 1, characterized in that the balloon can be filled with fluid via a closed channel at the distal end of the catheter.

10. The device in accordance with claim 1, characterized in that the balloon arrangement for closing off the urinal bladder and holding the catheter in the bladder lumen in the male device is formed by a first balloon at the proximal end and a second balloon located distally from the first balloon, which with the catheter in inserted condition, lies outside the bladder muscle.

11. The device in accordance with claim 1, characterized in that the balloon arrangement for closing off the urinal bladder and holding the catheter in the bladder lumen in the female device is formed by a first balloon at the proximal end and the actuating balloon.

12. The device in accordance with claim 11, characterized in that the actuating balloon has protrusions on its outer surface for fixing its position.

13. The device in accordance with claim 1, characterized in that the catheter consists of a proximal part and a distal part which are linked separably by a plugged connection and are held together by a tensile connection after separation of the plugged connected.

14. The device in accordance with claim 13, characterized in that the plugged connection surrounds small pipes extending from the proximal face end of the distal part which can be inserted into the openings of the channels at the distal end of the proximal part and form a continuation of these channels to the distal end of the catheter.

15. The device in accordance with claim 13, characterized in that the tensile connection between the proximal part and the distal part is formed by a thread whose length permits the separation of the plugged connection.

16. The device in accordance with claim 13, characterized in that a hooking element is attached to the distal end of the distal part in which an extraction instrument can engage during extraction of the device.

17. The device in accordance with claim 16, characterized in that the hooking element is formed by a thread spanned cross-wise over the distal catheter opening which, at the same time, forms a contact element for an insertion device during insertion of the catheter.

18. The device in accordance with claim 13 further comprising an insertion device for insertion of a device into the male urethra, with a shaft which can be pushed onto the distal end of the distal part, characterized in that a nucleus shaped rod is shiftably located in the shaft, the front end of which can be pushed out of the shaft to contact the distal end of the catheter.

19. The device in accordance with claim 18 wherein the front end section of the nucleus can be inserted into the lumen of the catheter up to a stop and in inserted condition reinforcingly bridges a joint in the catheter consisting of a proximal part and a distal part.

20. The device in accordance with claim 19 wherein the cross-section of the front end section is smaller than that of the nucleus and that the stop is a shoulder.

21. The device in accordance with claim 18 wherein the rear end of the nucleus shaped rod protrudes from the shaft as an actuating end.

22. The device in accordance with claim 18 wherein the insertion device is, at the same time, designed as a filling device to allow the balloons to be filled with fluid in that the front end of the shaft is designed as a plug connection with canulae which can be pushed into puncture valves in the face end of the catheter part.

23. A device for the treatment of human urinary incontinence to be used by a human being having a bladder and a urethra, comprising:
　a. a catheter having a proximal end with a tip and a distal end, which catheter is inserted into the urethra and is dimensioned such that its distal end in the inserted condition lies within the urethra and its proximal end in the inserted condition lies within the bladder;
　b. said catheter including a balloon arrangement which is filled with fluid to close off the urinary bladder and to hold said catheter in the lumen of the urethra, the fluid being admitted to and discharged from the balloon arrangement through at least one channel which is closed off at said distal end of said catheter;
　c. a valve mounted adjacent to said tip of said proximal end of said catheter and which is positioned inside the bladder to permit urine to be evacuated when the valve is opened; and
　d. means for opening said valve to permit urine to be discharged from the bladder while said catheter remains within the human body and means for closing said valve after the urine has been evacuated from the bladder;
　e. whereby said catheter can remain in the human body for the purposes of both closing of the flow of urine from the bladder and also permitting urine to be evacuated from the bladder while said catheter remains in its inserted condition.

24. The device in accordance with claim 23 wherein said balloon arrangement further comprises:
 a. a first balloon located adjacent to said proximal end and a second balloon located distally from the first balloon;
 b. means for inflating both balloons such that in the inflated condition said first and second balloons are located on opposite sides of the sphincter muscle and thereby maintain said catheter in the correct position.

25. The device in accordance with claim 24 wherein said means for inflating both balloons causes said first balloon to be inflated more rapidly than said second balloon.

26. The device in accordance with claim 25 wherein said means for inflating both balloons comprises at least one channel extending from said distal end of said catheter to a first opening located in said catheter and within said first balloon and a second opening located in said catheter, within said at least one channel and within said second balloon, where the first opening is larger than the second opening and said balloons are inflated through fluid entering from said distal end of said catheter, flowing through said at least one channel, and into the respective balloons through their respective openings.

27. The device in accordance with claim 25 wherein said means for inflating both balloons comprises a first channel extending from said distal end of said catheter to a first opening located in said catheter and within said first balloon, and a second channel extending from a second opening in said catheter and within said first balloon to a third opening located in said catheter and within said second balloon, where the second opening is larger than the third opening and said balloons are inflated through fluid entering from said distal end of said catheter into the first channel, flowing through the first channel into said first balloon from the first opening and then from the second opening into the second channel and into said second balloon through the third opening.

28. The device in accordance with claim 24 wherein said second balloon also functions as an actuating element.

29. The device in accordance with claim 28 wherein said means for inflating both balloons causes said first balloon to be inflated more rapidly than said second balloon.

30. The device in accordance with claim 29 wherein said means for inflating both balloons comprises at least one channel extending from said distal end of said catheter to a first opening located in said catheter and within said first balloon and a second opening located in said catheter, within the at least one channel and within said second balloon, where the first opening is larger than the second opening and said balloons are inflated through fluid entering from said distal end of said catheter, flowing through the at least one channel, and into the respective balloons through their respective openings.

31. The device in accordance with claim 23 wherein said valve is formed by a diagonal cut on said proximal end of said catheter.

32. The device in accordance with claim 23 wherein said means for opening said valve to permit urine to be discharged from the bladder further comprises:
 a. an actuating element located adjacent to said distal end of said catheter;
 b. at least one channel extending from said actuating element to a semi-balloon located adjacent to said tip of said proximal end of said catheter; and
 c. a tissue element covering a portion of said semi-balloon;
 d. whereby said actuating element causes said semi-balloon to inflate which in turn moves said tissue element which causes said valve to open.

33. The device in accordance with claim 32 wherein said actuating element is a balloon which is inflated by fluid and which is actuated by a force exerted on said balloon which causes the fluid to flow through said at least one channel, and into said semi-balloon to inflate said semi-balloon.

34. The device in accordance with claim 32 further comprising ribs molded into the surface of said balloon of said actuating element.

35. The device in accordance with claim 23 wherein said catheter further comprises a proximal part having the proximal end and a distal part having the distal end, wherein said proximal part and said distal part are separable and are held together by connecting means and when pulled apart still maintain a loose connection through thread means attached to the respective parts.

36. The device in accordance with claim 23 wherein said catheter has a lumen running from said proximal end to said distal end and said distal end further comprises a transverse thread means within the lumen to facilitate insertion and removal of said catheter.

37. A male device for the treatment of human urinary incontinence to be used by a human being having a bladder, a urethra, a sphincter muscle, and a penis, comprising:
 a. a catheter having a proximal end with a tip and a distal end with the length of the catheter dimensioned such that in its inserted condition, the distal end lies within the urethra and the tip of the proximal end lies within the bladder;
 b. a balloon arrangement including a first balloon located adjacent to said proximal end, a second balloon located distally from the first balloon, and means for inflating both balloons such that in the inflated condition the first and second balloons are located on opposite sides of the sphincter muscle;
 c. a valve located adjacent to said proximal end of said catheter and situated closer to said tip of said proximal end than said first balloon, with the valve situated within the bladder such that urine can be evacuated from the bladder when the valve is opened;
 d. said valve communicating with a lumen within said catheter which permits urine to flow from the opened valve, through the lumen and into the urethra;
 e. urine is prevented from evacuating the bladder when said first balloon is in the inflated condition and said valve is closed; and
 f. valve actuating means located adjacent to said distal end of said catheter and positioned within the urethra such that the valve actuating means is actuated through external pressure on the penis which is transmitted through the urethral wall to the valve actuating means to open said valve and permit urine to be evacuated;
 g. whereby said catheter remains within the human body both during the period that urine is prevented from being evacuated from the bladder by the inflated first balloon and during the period that urine is evacuated from the bladder by exiting through the opened valve.

38. The male device in accordance with claim 37 wherein said means for inflating said first balloon and said second balloon such that said first balloon is inflated more rapidly than said second balloon.

39. The male device in accordance with claim 38 wherein said means for inflating both balloons comprises at least one channel extending from said distal end of said catheter to a first opening located in said catheter and within said first balloon and a second opening located in said catheter, within the at least one channel and within said second balloon, where the first opening is larger than the second opening and said balloons are inflated through fluid entering from said distal end of said catheter, flowing through the at least one channel, and into the respective balloons through their respective openings.

40. The male device in accordance with claim 38 wherein said means for inflating both balloons comprises a first channel extending from said distal end of said catheter to a first opening located in said catheter and within said first balloon, and a second channel extending from a second opening in said catheter and within said first balloon to a third opening located in said catheter and within said second balloon, where the second opening is larger than the third opening and said balloons are inflated through fluid entering from said distal end of said catheter into the first channel, flowing through the first channel into said first balloon from the first opening and then from the second opening into the second channel and into said second balloon through the third opening.

41. The male device in accordance with claim 37 wherein said valve is formed by a diagonal cut on said proximal end of said catheter.

42. The male device in accordance with claim 37 wherein said valve actuating means for opening said valve to permit urine to be discharged from the bladder further comprises:
   a. an actuating element located adjacent to said distal end of said catheter;
   b. at least one channel extending from said actuating element to a semi-balloon located adjacent to said tip of said proximal end of said catheter; and
   c. a tissue element covering a portion of said semi-balloon;
   d. whereby said actuating element causes said semi-balloon to inflate which in turn moves said tissue element which causes said valve to open.

43. The male device in accordance with claim 42 wherein said actuating element is a balloon which is inflated by fluid and which is actuated by a force exerted on said balloon which causes the fluid to flow through said at least one channel, and into said semi-balloon to inflate said semi-balloon.

44. The male device in accordance with claim 37 wherein said catheter further comprises a proximal part having the proximal end and a distal part having the distal end, wherein said proximal part and said distal part are separable and are held together by connecting means and when pulled apart still maintain a loose connection through thread means attached to the respective parts.

45. The male device in accordance with claim 37 wherein said catheter has a lumen running from said proximal end to said distal end and said distal end further comprises a transverse thread means within the lumen to facilitate insertion and removal of said catheter.

46. A female device for the treatment of human urinary incontinence to be used by a human being having a bladder, a urethra, a sphincter muscle, a vagina and a symphysis, comprising:
   a. a catheter having a proximal end with a tip and a distal end with the length of the catheter dimensioned such that in its inserted condition, the distal end lies within the urethra and the tip of the proximal end lies within the bladder;
   b. an arrangement including a balloon located adjacent to said proximal end, valve actuating means located distally from the balloon, and means for inflating both the balloon and the valve actuating means such that in the inflated condition the balloon and the valve actuating means are located on opposite sides of the sphincter muscle;
   c. a valve located adjacent to said proximal end of said catheter and situated closer to said tip of said proximal end than said balloon, with the valve situated within the bladder such that urine can be evacuated from the bladder when the valve is opened;
   d. said valve communicating with a lumen within said catheter which permits urine to flow from the opened valve, through the lumen and into the urethra;
   e. urine is prevented from evacuating the bladder when said balloon is in the inflated condition and said valve is closed; and
   f. said valve actuating means located adjacent to the symphysis and positioned such that pressure from a finger inserted into the vagina and pressing against said valve actuating means to force it against the symphysis causes said valve to open and permit urine to be evacuated;
   g. whereby said catheter remains within the human body both during the period that urine is prevented from being evacuated from the bladder and during the period that urine is evacuated from the bladder by exiting through the opened valve.

47. The female device in accordance with claim 46 wherein said means for inflating both said balloon and said valve actuating means causes said balloon to be inflated more rapidly than said valve actuating means.

48. The female device in accordance with claim 47 wherein said means for inflating the balloon and said valve actuating means comprises at least one channel extending from said distal end of said catheter to a first opening located in said catheter and within said balloon and a second opening located in said catheter, within the at least one channel and within said valve actuating means, where the first opening is larger than the second opening and said balloon and said valve actuating means are inflated through fluid entering from said distal end of said catheter, flowing through the at least one channel, and into the respective balloon and valve actuating means through their respective openings.

49. The female device in accordance with claim 46 wherein said valve is formed by a diagonal cut on said proximal end of said catheter.

50. The female device in accordance with claim 46 wherein said means for opening said valve to permit urine to be discharged from the bladder further comprises:
   a. an actuating element located adjacent to said distal end of said catheter;
   b. at least one channel extending from said actuating element to a semi-balloon located adjacent to said tip of said proximal end of said catheter; and
   c. a tissue element covering a portion of said semi-balloon;
   d. whereby said actuating element causes said semi-balloon to inflate which in turn moves said tissue element which causes valve to open.

51. The female device in accordance with claim 50 wherein said actuating element is a balloon which is inflated by fluid and which is actuated by a force exerted on said balloon which causes the fluid to flow through said at least one channel, and into said semi-balloon to inflate said semi-balloon.

52. The female device in accordance with claim 51 further comprising ribs molded into the surface of said balloon of said actuating element.

53. The female device in accordance with claim 46 wherein said catheter further comprises a proximal part having the proximal end and a distal part having the distal end, wherein said proximal part and said distal part are separable and are held together by connecting means and when pulled apart still maintain a loose connection through thread means attached to the respective parts.

54. The female device in accordance with claim 46 wherein said catheter has a lumen running from said proximal end to said distal end and said distal end further comprises a transverse thread means within the lumen to facilitate insertion and removal of said catheter.

55. The female device in accordance with claim 46 wherein said valve actuating means also functions as a second balloon to maintain said catheter in the correct position within the body.

* * * * *